United States Patent
Wilke et al.

(10) Patent No.: US 11,786,385 B2
(45) Date of Patent: Oct. 17, 2023

(54) OSSEOINTEGRATION SYSTEM

(71) Applicant: Mayo Foundation for Medical Education and Research, Rochester, MN (US)

(72) Inventors: Benjamin K. Wilke, Ponte Verde Beach, FL (US); Shawn P. Robinson, Fleming Island, FL (US); James M. Jeter, Jacksonville, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 39 days.

(21) Appl. No.: 17/486,291

(22) Filed: Sep. 27, 2021

(65) Prior Publication Data

US 2022/0096250 A1  Mar. 31, 2022

Related U.S. Application Data

(60) Provisional application No. 63/084,235, filed on Sep. 28, 2020.

(51) Int. Cl.
  *A61F 2/78* (2006.01)
  *A61F 2/50* (2006.01)
  *A61F 2/28* (2006.01)
  *A61F 2/30* (2006.01)

(52) U.S. Cl.
  CPC .............. *A61F 2/78* (2013.01); *A61F 2/2814* (2013.01); *A61F 2002/3085* (2013.01); *A61F 2002/3093* (2013.01); *A61F 2002/30224* (2013.01); *A61F 2002/30553* (2013.01); *A61F 2002/30894* (2013.01); *A61F 2002/5007* (2013.01); *A61F 2002/7887* (2013.01)

(58) Field of Classification Search
  CPC .. A61F 2/2814; A61F 2/78; A61F 2/80; A61F 2002/30224; A61F 2002/30553; A61F 2002/3085; A61F 2002/30894; A61F 2002/3093; A61F 2002/5007; A61F 2002/7887
  See application file for complete search history.

(56) References Cited

U.S. PATENT DOCUMENTS

| | | |
|---|---|---|
| 4,822,363 A | 4/1989 | Phillips |
| 7,033,400 B2 | 4/2006 | Currier |
| 9,668,889 B2 | 6/2017 | Holt et al. |

(Continued)

FOREIGN PATENT DOCUMENTS

| | | | | |
|---|---|---|---|---|
| CN | 205729542 U | * | 11/2016 | |
| WO | WO-2017120484 A1 | * | 7/2017 | ............... A61F 2/64 |

OTHER PUBLICATIONS

"Compress Compliant Pre-stress Device Orthopaedic Salvage System", Surgical Technique, Biomet, 2014, 78 pages.

(Continued)

*Primary Examiner* — Christie Bahena

(57) ABSTRACT

Improved osseointegration devices and structures, including such structures that can be used in connection with prosthetic limbs. Examples include a self-centering implant/nut configuration, a centering device, a tapered mounting screw hole, a coupling device, and an aiming device. The devices are highly efficacious. For example, they can be secured with minimal residual bone, and may be removed without significant bone destruction.

18 Claims, 14 Drawing Sheets

(56) References Cited

U.S. PATENT DOCUMENTS

| | | | |
|---|---|---|---|
| 2014/0195002 A1* | 7/2014 | Bachus | A61F 2/78 |
| | | | 623/23.44 |
| 2014/0228973 A1* | 8/2014 | Porter | A61F 2/2814 |
| | | | 623/33 |
| 2015/0140508 A1* | 5/2015 | Nike | A61C 8/005 |
| | | | 433/172 |
| 2021/0077282 A1* | 3/2021 | Radzinsky | A61F 2/76 |

OTHER PUBLICATIONS

Hoellwarth et al., "Osseointegration for Amputees Current Implants, Techniques, and Future Directions", JBJS Reviews, vol. 8, No. 3, 2020, e0043, pp. 1-10.

Thesleff et al., "Biomechanical Characterisation of Bone-anchored Implant Systems for Amputation Limb Prostheses: A Systematic Review", Ann Biomed Eng., vol. 46, No. 3, 2018, pp. 377-391.

Zaid et al., "Orthopaedic Osseointegration: State of the Art", J. Am. Acad. Orthop. Surg., vol. 27, No. 22, Nov. 15, 2019, pp. e977-e985.

* cited by examiner

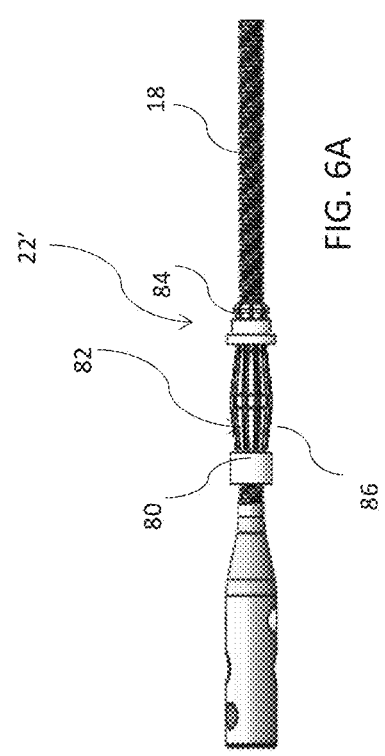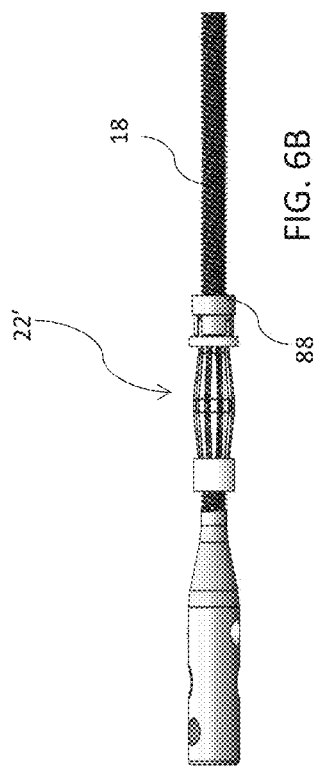

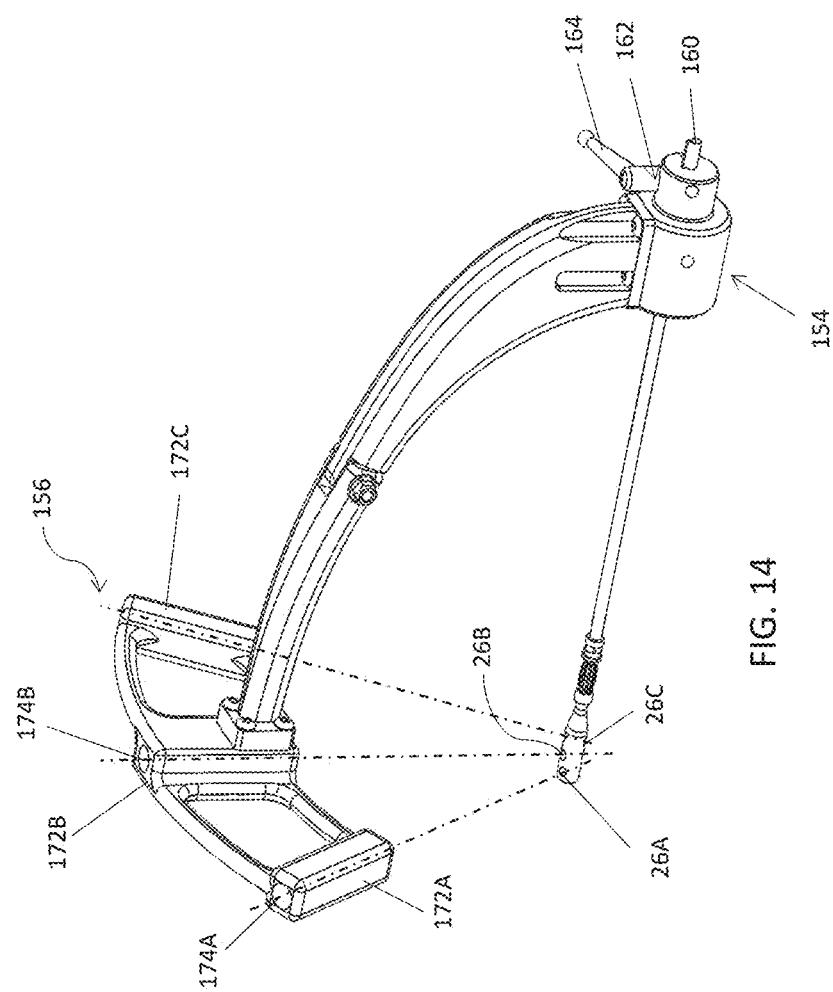

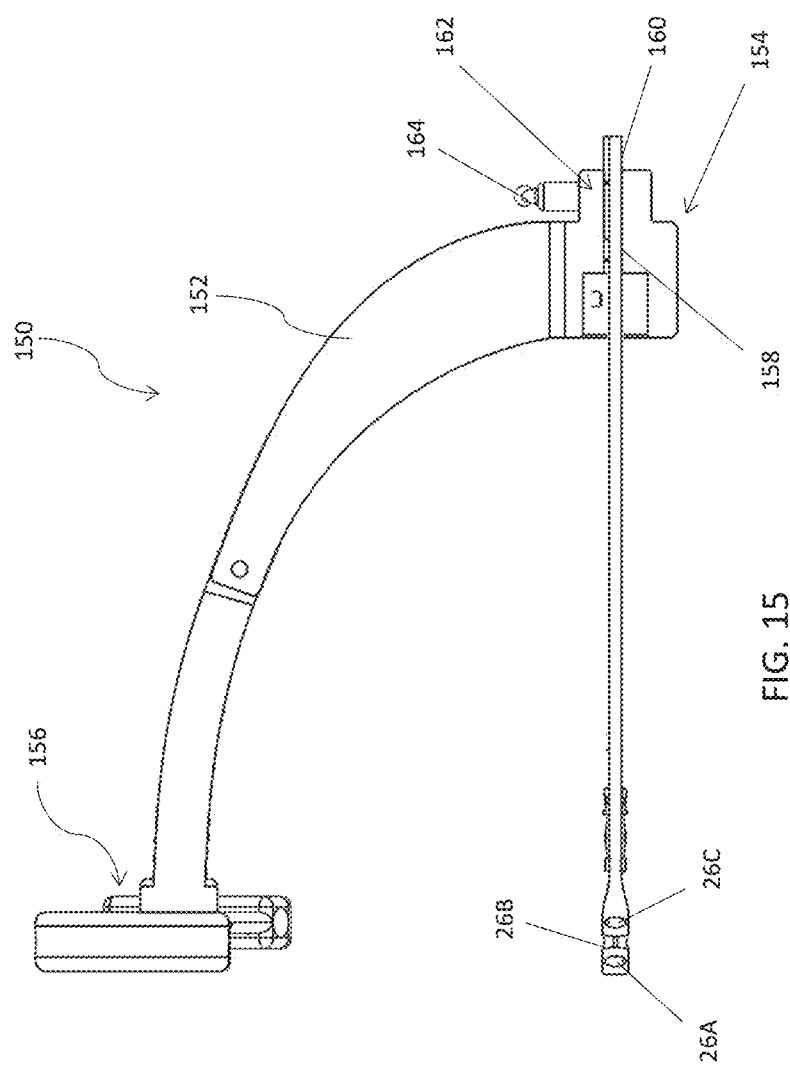

OSSEOINTEGRATION SYSTEM

CROSS-REFERENCE TO RELATED APPLICATION

This application claims the benefit of Provisional Application No. 63/084,235, filed Sep. 28, 2020, which is incorporated herein by reference in its entirety for all purposes.

FIELD

This disclosure relates generally to osseointegration systems including implants. The disclosure also relates to coupling structures for coupling structures such as prosthetic limbs to osseointegration implants.

BACKGROUND

Patients with amputations often use prosthetic limbs having a socket. The socket includes a suction-type seal for attachment to the amputation site. Prosthetic limb attachment structures of these types may be susceptible to limitations such as wound issues, loss of suction, volume changes of the residual limb and difficulties fitting the socket over short residual limbs.

Osseointegration, a connection of a prosthetic implant to a bone of the residual limb, is generally known. Osseointegration systems include the Integrated Leg Prosthesis (ILP), and Osseointegrated Prosthetic Limb (OLP). The Compress device also includes osseointegration structures.

There remains, however, a continuing need for improved osseointegration structures. For example, there is a need for improved osseointegration structures for use in connection with prosthetic limbs.

SUMMARY

Described examples and embodiments include improved osseointegration devices and structures, including such structures that can be used in connection with prosthetic limbs. The devices are highly efficacious. For example, they can be secured with minimal residual bone, and may be removed without significant bone destruction.

One example includes a self-centering/nut configuration. An exemplary osseointegration system may comprise: a rod configured for placement in a bone cavity, including: a proximal mounting portion configured to be secured to the bone in the bone cavity; and a threaded distal portion; an implant including: a first surface configured to engage an end of the bone; a second surface; and an aperture through the implant, wherein the aperture is configured to enable the rod to extend through the implant; a threaded first nut, including: a first end face; a second end portion; and a threaded aperture through the nut configured to be received by the threaded distal portion of the rod; wherein the rod, implant and first nut are configured to cause the first end face of the first nut to engage the second surface of the implant and to compress the first surface of the implant onto the end of the bone when the threaded aperture of the first nut is mounted to the threaded distal portion of the rod.

In some embodiments: the second surface of the implant tapers in a direction away from the first surface with increasing distance from the aperture through the implant; and the first end face of the first nut tapers in a direction toward the second end portion with increasing distance from the aperture through the first nut. In some embodiments, the second surface of the implant and the first end face of the first nut include complementary engaging surfaces. In some embodiments, a diameter of a portion of the rod extending through the aperture of the implant is sufficiently less than a diameter of the aperture of the implant to allow self-centering angular motion between the implant and the rod. Some embodiments further include a second nut configured to be mounted to the threaded distal portion of the rod opposite the first nut from the implant and to engage the second end portion of the first nut.

Another example includes a centering device. An exemplary osseointegration system may comprise: a rod configured for placement in a bone cavity having a diameter, including: a proximal mounting portion configured to be secured to the bone in the bone cavity; and a distal portion; an implant, including: a proximal surface configured to engage an end of the bone; a second surface; an aperture through the implant, wherein the aperture is configured to enable the rod to extend through the implant; a fastening structure to secure the implant to the distal portion of the rod, wherein the fastening structure is configured to compress the proximal surface of the implant onto the end of the bone; and a diametrically adjustable centering device on a portion of the rod configured to be located within the bone cavity, wherein the centering device is adjustable between a first diameter less than or equal to the diameter of the bone cavity to a second diameter at least as great as the diameter of the bone cavity.

In some embodiments, the centering device is configured to be expandable between the first diameter and the second diameter after the rod is inserted into the bone cavity. In some embodiments, the centering device includes: a first end portion configured to be mounted to the rod; a diametrically expandable member mounted to the first end portion; and a second end portion mounted to the diametrically expandable member opposite the diametrically expandable member from the first end portion, wherein the second end portion is configured to move from a first position on the rod in a direction toward the first end portion to a second position on the rod and to diametrically expand the expandable member. Some embodiments further include a clamping member to clamp the second end portion of the centering device to the rod at the second location. In some embodiments, the centering device is configured to be compressible from the second diameter to the diameter of the bone cavity during insertion of the centering device into the bone cavity. In some embodiments, the centering device includes diametrically compressible portions extending from the rod at circumferentially-spaced locations. In some embodiments, the diametrically compressible portions include a plurality of fingers. In some embodiments: the centering device further includes a mounting member configured to be mounted to the rod; and the fingers extend from the mounting member, and are configured to be deformed from the second diameter to the diameter of the bone cavity during insertion of the centering device into the bone cavity.

Another example includes a tapered mounting screw hole. An exemplary osseointegration system may comprise: a rod configured for placement in a bone cavity having a diameter, including: a proximal mounting portion configured to be secured to the bone in the bone cavity; and a distal portion; an implant including: a proximal surface configured to engage an end of the bone; a second surface; an aperture through the implant, wherein the aperture is configured to enable the rod to extend through the implant; a fastening structure to secure the implant to the distal portion of the rod, wherein the fastening structure is configured to compress the proximal surface of the implant onto the end of the bone; and a first mounting aperture through the proximal mounting portion of the rod for receiving a first shaft having a first diameter extending through the bone to secure the rod in the bone cavity, wherein the first mounting aperture includes a varying diameter portion to enable pivotal motion of the rod on the first shaft and enable the rod to center in the bone cavity.

In some embodiments, the first mounting aperture includes a first tapered portion tapering from a first diameter greater than the diameter of the first shaft to a second diameter greater than the diameter of the first shaft, wherein the first diameter is greater than the second diameter. In some embodiments: the first tapered portion of the first mounting aperture extends into the proximal mounting portion of the rod from a first side of the rod, and tapers from the first diameter to the second diameter with increasing distance from the first side of the rod; and the first mounting aperture further includes a second tapered portion extending into the proximal mounting portion of the rod from a second side of the rod, and wherein the second tapered portion tapers from a third diameter greater than the diameter of the first shaft (and optionally equal to the first diameter of the first tapered portion) to the second diameter with increasing distance from the second side of the rod. In some embodiments, the first mounting aperture allows pivotal motion of the rod up to +/−7.5 degrees with respect to the first shaft. Some embodiments further comprise the first shaft, and wherein the first shaft optionally includes a screw having a head and threads configured to engage the bone. Some embodiments further include a second mounting aperture through the proximal mounting portion of the rod for receiving a second shaft extending through the bone to secure the bone in the bone cavity, wherein the second mounting aperture has a constant diameter.

Another example is a coupling device. An exemplary osseointegration system, comprises: an implant including an outer side surface; an osseointegration mount for mounting the implant to a bone; and a coupling device coupled to the implant, the coupling device including: a base; a plurality of members extending from the base at circumferentially-spaced locations and configured to engage the outer side surface of the implant; and one or more bias members releasably forcing the plurality of members into engagement with the outer side surface of the implant.

In some embodiments, at least some of the members include an elongated finger. In some embodiments, each elongated finger includes a proximal end portion pivotally connected to the base. In some embodiments, each elongated finger includes a distal end portion. In some embodiments: each finger is configured to receive a resilient band; and the one or more bias members includes at least one resilient band engaging the fingers to bias the fingers into engagement with the side surface of the implant. In some embodiments, the distal end portions of the fingers define a circumferential recess around an exterior of the coupling device, and wherein the circumferential recess is configured to receive the at least one resilient band. In some embodiments, the distal end portions of the fingers include recesses for receiving the at least one resilient band. In some embodiments: the outer side surface of the implant includes one or more flat surface portions; and at least some of the members include interior flat surface portions configured to engage and mate with one of the one or more flat surface portions of the implant. In some embodiments: the outer side surface of the implant includes one or more convex surface portions; and at least some of the members include interior concave surface portions configured to engage and mate with one of the one or more convex surface portions of the implant. Some embodiments further include a peripheral device, optionally a limb prosthesis, coupled to the coupling device.

Still other embodiments include the coupling device alone (i.e., without the implant and osseointegration mount). Still other embodiments include the implant alone (i.e., without the osseointegration mount and coupling device). In some embodiments, the implant includes an implant member and an end cap on the implant member, and wherein the coupling device is configured to engage the end cap.

Another example includes an aiming device. An exemplary aiming device for use in connection with an osseointegration system may include a rod of the type including a distal end and a mounting aperture for receiving a shaft extending through a bone, the aiming device comprising: a body including first and second portions; an engagement structure on the first portion of the body, wherein the engagement structure is configured to receive the rod; and a drill guide including an elongated aperture on the second portion of the body; and wherein the body, engagement structure and drill guide are configured such that the elongated aperture on the drill guide is colinear with the mounting aperture on the rod when the engagement structure receives the rod.

In some embodiments, the engagement structure comprises a clamp to releasably clamp the rod to the body. In some embodiments, the engagement structure includes a rotational registration structure configured to cooperate with the rod to receive the rod in a predetermined rotational orientation. In some embodiments, the engagement structure includes a length registration structure configured to cooperate with the rod and receive the rod at a predetermined axial position. Some embodiments further include the rod. In some embodiments, the rod includes a rotational registration structure configured to cooperate with the engagement structure of the aiming device so the rod is in a predetermined rotational orientation when received by the engagement structure. In some embodiments, the rod includes a length registration structure configured to cooperate with the engagement structure of the aiming device so the rod is located at a predetermined axial location when received by the engagement structure. In some embodiments, the registration structure comprises a keyway. In some embodiments, the keyway comprises an aperture and a key extending into the aperture. Some embodiments further include the rod, wherein the rod includes a slot configured to be received by the key.

Another example includes implant feature combinations. An exemplary osseointegration system comprises: a rod configured for placement is a bone cavity, including: a proximal mounting portion configured to be secured to the bone in the bone cavity; and a distal portion; and an implant, including: a first surface configured to engage an end of the bone; a second surface; and an aperture through the implant, wherein the aperture is configured to enable the rod to extend through the implant; and any one or more of the following features A-D: A. a threaded distal portion on the rod; a threaded first nut, including: a first end face; a second end portion; and a threaded aperture through the nut configured to be received by the threaded distal portion of the rod; and wherein the rod, implant and first nut are configured to cause the first end face of the first nut to engage the second surface of the implant and to compress the first surface of the implant onto the end of the bone when the threaded aperture of the first nut is mounted to the threaded distal portion of the rod; and/or B. a diametrically adjustable centering device on a portion of the rod configured to be located within the bone cavity, wherein the centering device is adjustable between a first diameter less or equal to the diameter of the bone cavity to a second diameter at least as great as the diameter of the bone cavity; and/or C. a first mounting aperture through the proximal mounting portion of the rod for receiving a first shaft having a first diameter extending through the bone to secure the rod in the bone cavity, wherein the first mounting aperture includes a varying diameter portion to enable pivotal motion of the rod on the first shaft and enable the rod to center in the bone cavity; and/or D. the implant including an outer side surface; and a coupling device coupled to the implant, the coupling device including: a base; a plurality of members extending from the base at circumferentially-spaced locations and configured to engage the outer side surface of the implant; and one or more bias members releasably forcing the plurality of members into engagement with the outer side surface of the implant.

BRIEF DESCRIPTION OF THE DRAWINGS

FIG. 6A is a side view of an another embodiment of a centering device on the rod in a reduced diameter insertion state, in accordance with embodiments.

FIG. 6B is a side view of the centering device shown in FIG. 6A on the rod, with a deployment structure.

FIG. 12A illustrates sides where the coupling device is mounted to spherical surfaces of the implant, and FIG. 12B illustrates sides where the coupling device is mounted to flat surfaces of the implant.

FIGS. 13 and 14 are isometric illustrations of an aiming arm in accordance with embodiments, shown with the rod of the osseointegration system registered and seated in the aiming arm. The implant is shown mounted to the bone in FIG. 13.

FIG. 15 is a partial cross sectional side view of the aiming arm shown in FIGS. 13 and 14, in accordance with embodiments.

DETAILED DESCRIPTION

Figure 1:
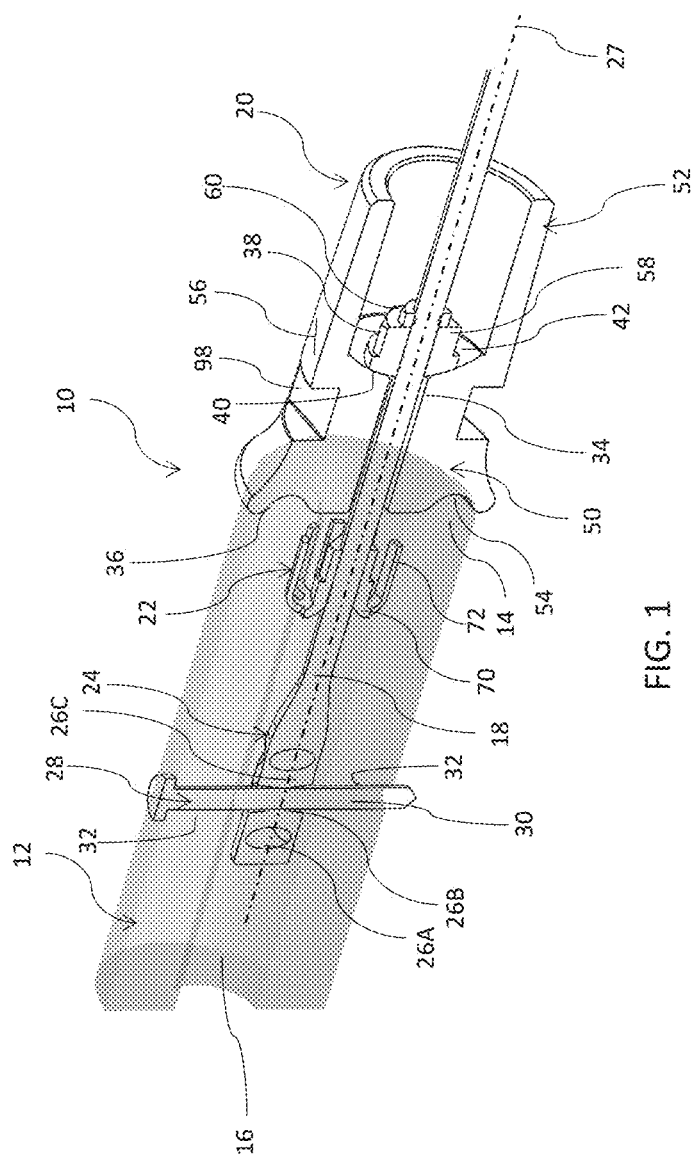
FIG. 1 is cross sectional isometric view of portions of an osseointegration system, including a rod, centering device and implant, in accordance with embodiments mounted to a bone.
Figure 2:
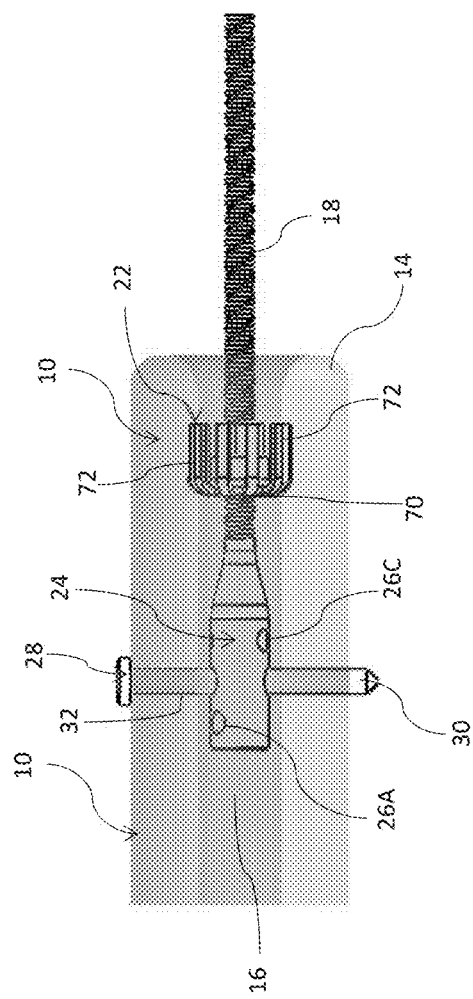
FIG. 2 is a side view of portions of the osseointegration system shown in FIG. 1, including the rod and centering device, mounted to the bone, where the bone is shown in cross section.
Figure 3:
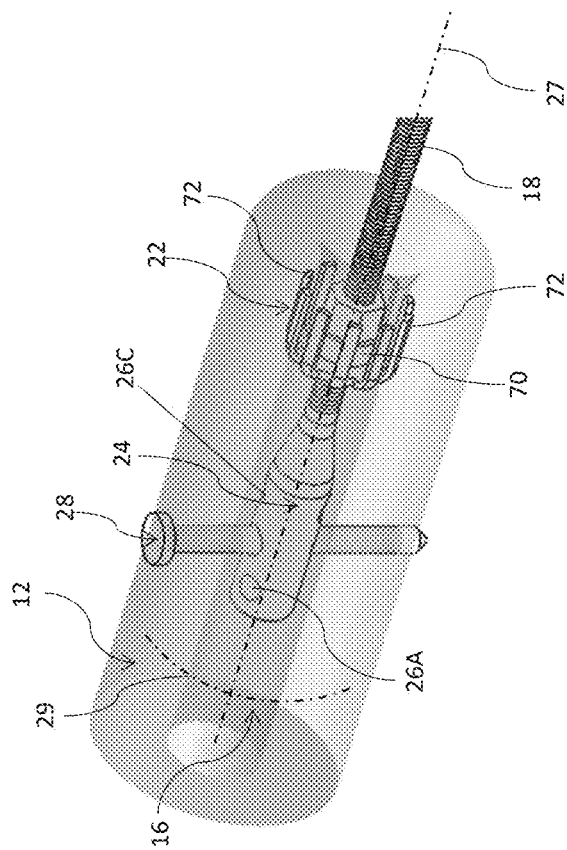
FIG. 3 is an isometric view of portions of the osseointegration system shown in FIG. 1, including the rod and centering device, mounted to the bone, with portions of the bone shown in phantom.

FIGS. 1-3 illustrate portions of an osseointegration system 10 in accordance with embodiments mounted to a bone 12 of a patient. As shown, the bone 12 includes a distal end 14 and a cavity 16. Osseointegration system 10 includes rod 18 and implant 20. A centering device 22 is located on rod 18 in the illustrated embodiments. Rod 18 includes a mounting portion 24 on its proximal end that is configured to be mounted to the bone 12 within the cavity 16. The centering device 22, which is positioned on the rod 18 at a location distal to the mounting portion 24, engages the bone 12 within the cavity 16 and positions the rod at a relatively central location within the cavity. Rod 18 extends through an aperture 34 in the implant 20 when the implant is mounted to the distal end 14 of the bone 12. A threaded first nut 38 cooperates with threads on the rod 18 to secure the implant 20 to the rod and provide compression of the implant onto the bone 12. As described below, peripheral devices such as prostheses can be coupled to the implant 20.

Portions of the rod 18 distal from the mounting portion 24 that receive the implant 20 and/or centering device 22 are threaded in the illustrated embodiment to provide fastening systems for the implant and centering device. Other embodiments may include other structures that cooperate with the implant 20 and/or centering device 22 to secure those components to the rod 18 and provide the functionality described herein. Mounting portion 24 is sized and/or otherwise configured to be received within the cavity 16 of the bone 12 and includes one or more apertures 26A-26C therethrough. The three apertures 26A-26C are spaced apart from one another along a longitudinal axis 27 of the rod 18 and implant 20. In the illustrated embodiments the apertures 26A-26C extend through the rod 18 at perpendicular angles with respect to the longitudinal axis 27, and that are rotationally offset from one another about a circumferential axis 29. One or more pins 28 (one is shown for purposes of example) including shafts 30 extend through apertures 32 in the bone 12 and the apertures 26A-26C in the mounting portion 24 of the rod 18 to secure the rod to the bone. Other embodiments include more or fewer apertures 26A-26C, and the apertures may be arranged in other configurations. Yet other embodiments include other structures for securing the rod 18 to the bone 12.

Implant 20 includes a first or proximal end surface 36 configured to engage the end 14 of the bone 12, and a second surface 42. The first nut 38 includes a threaded aperture that is received by the threaded rod 18 and a first or proximal end face 40 that engages the second surface 42 of the implant 20. The threaded rod 18 and first nut 38 function as a fastening structure to compress and secure the implant 20 onto the end 14 of the bone 12.

Implant 20 includes a base portion 50 and a mounting portion 52. In the illustrated embodiment the proximal end surface 36 of the implant 20 is located on the proximal end of the base portion 50 and includes an annular recess or groove 54 that is configured to receive the end 14 of the bone 12. Portions of the proximal end surface 36 configured to engage the bone 12 may include structures or coatings (not shown) to enhance bone growth. The second surface 42 of the implant 20 is located on a distal side of the base portion 50 in the illustrated embodiments. In the illustrated embodiments the surface 42 tapers in a direction away from the proximal end of the base portion 50 with increasing distance from the aperture 34 to provide a generally concave and optionally spherical surface. Mounting portion 52 is a generally tubular member extending distally from the distal side of the base portion 50, and includes a generally cylindrical outer surface 56. In embodiments, the outer surface 56 tapers in a direction toward a center of the mounting portion 52 with increasing distance from the base portion 50 (i.e., the outer diameter of the mounting portion 52 decreases with increasing distance from the base portion). As described below, the tapered outer surface 56 provides a mounting system, such as a Jacobs or other machine taper, to receive and secure other components such as peripheral devices to the implant 20.

The proximal end face 40 of first nut 38 tapers in a direction toward a distal end portion 58 of the first nut with increasing distance from its threaded aperture. In embodiments, the tapered or spherical proximal end face of the first nut 38 is complementary to the tapered or spherical surface 42 on the base portion 50. In embodiments, the outer diameter of the portions of the rod 18 that extend through the aperture 34 of the implant 20 is less than the diameter of the aperture 34 by a sufficient amount to accommodate limited angular motion and positioning of the rod with respect to the implant when the implant is seated onto the bone 12 (e.g., if the rod and/or aperture are not centered on and/or perpendicular to a central longitudinal axis of the bone). The complimentary tapered or spherical surfaces 40 and 42 of the first nut 38 and implant 20, respectively, allow self-centering engagement of the first nut and implant to accommodate any such angular and/or off center seating of the implant on the bone 12. The embodiments illustrated in FIG. 1 include a second or locking nut 60 that is threadedly received on the rod 18 opposite the first nut 38 from the implant 20 to retain the first nut on the rod.

Figure 4:
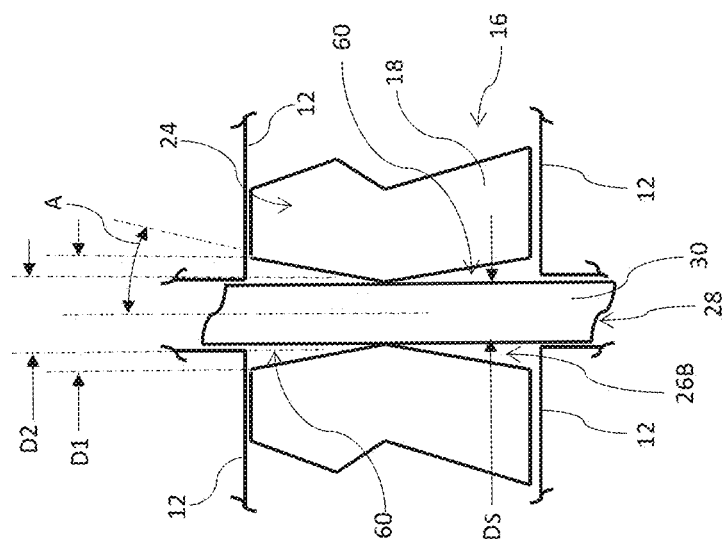
FIG. 4 is a detailed illustration of a portion of the mounting portion of the rod of the osseointegration system in accordance with embodiments, shown mounted to the bone.

FIG. 4 is a detailed illustration of a portion of the mounting portion 24 of the rod 18 secured to the bone 12 by a pin 28 in accordance with embodiments. The illustrated embodiments of the mounting portion 24 are configured to accommodate the relatively limited amounts of angular positioning of the rod 18 with respect to the bone 12 and enhance the self-centering capability described above. As shown, at least one of the apertures (26B in the illustrated embodiments) through the mounting portion 24 has a varying diameter portion 60. The embodiments illustrated in FIG. 4 have two varying diameter portions 60, each of which tapers from a first diameter D1 at the outer side of the rod 18 to a second diameter D2 within the rod about an angle A with respect to a longitudinal axis of the pin 28, where the diameter D2 is less than the diameter D1. Both diameters D1 and D2 are greater than the diameter DS of the shaft 30. The pin 28 therefore engages the rod 18 to secure the rod within the bone 12 and provide a support for the compression of the implant 20, while enabling the limited rotational movement and positioning of the rod within the cavity 16 of the bone 12. In embodiments, one or more of the varying diameter portions 60 of the aperture 26B is configured to allow +/−7.5 degrees of motion of the rod 18 relative to the pin 28. In embodiments, pin 28 is a screw including a head and threads on the shaft 30.

Centering device 22 is a diametrically adjustable member that aids in the positioning of the rod 18 within the cavity 16 of the bone 12. As described below, the centering device 22 is adjustable between a first diameter that is less than or equal to the diameter of the cavity 16 and a second diameter that is greater than the first diameter. In embodiments, the second diameter is at least as great as the diameter of the cavity 16, and in embodiments greater than the diameter of the cavity. In embodiments, the centering device 22 is configured to be adjusted to a diameter at which it engages the interior surface of the bone 12 and positions the rod 18 at or relatively near a diametric center of the cavity 16. Centering device 22 can thereby enhance the self-centering functionality of the implant 20 and first nut 38 described above.

Figure 5:
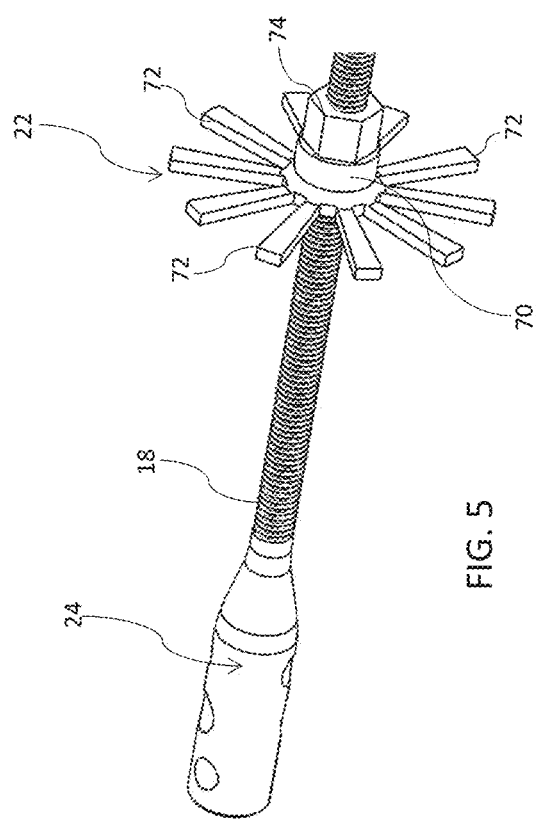
FIG. 5 is an isometric illustration of the centering device shown in FIGS. 1-3 in an enlarged diameter neutral state before insertion of the rod and centering device into the bone, in accordance with embodiments.
Figure 8:
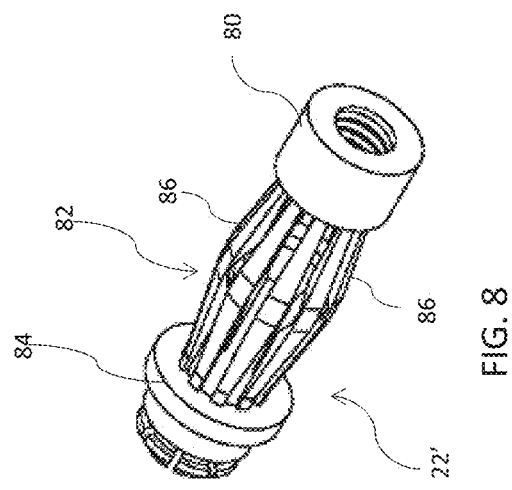
FIG. 8 is an isometric illustration of the centering device shown in FIGS. 6A, 6B and 7 in the reduced diameter insertion state, in accordance with embodiments.

FIGS. 1-3 illustrate an embodiment of the centering device 22 in a reduced diameter, deployed state within the cavity 16 of the bone 12 following insertion of the rod 18 with the centering device into the bone. FIG. 5 is an illustration of the embodiments of the centering device 22 shown in FIGS. 1-3 in an enlarged diameter, neutral or undeployed state before insertion of the rod 18 and centering device into the bone 12. The centering device 22 is configured to adjust by deforming or compressing from the enlarged diameter state shown in FIG. 5 to the reduced-diameter state shown in FIGS. 1-3 during insertion of the centering device into the cavity 16 from the distal end 14 of the bone 12. In the illustrated embodiments the centering device 22 includes a mounting member 70 configured to be mounted to the rod 18 and a plurality of fingers 72 extending radially from the mounting member at circumferentially spaced locations. In embodiments, the mounting member 70 is a threaded member in the form of a nut that can be screwed onto and positioned at a desired location along a length of the threaded rod 18. Other embodiments include other structures for fastening the mounting member 70 and/or fingers 72 to the rod 18.

Fingers 72 are deformable or compressible from the enlarged diameter state shown in FIG. 5 to the reduced diameter state shown in FIGS. 1-3. In embodiments, one or more of the fingers 72 includes one or more deformable sections that are configured to enable the fingers to bend and collapse to the reduced diameter state during insertion of the rod 18 into the bone 12. Alternatively or in addition, one or more of the fingers 72 are configured to deform along their entire lengths. During insertion of the rod 18 into the bone 12, the fingers 72 engage the end 14 of the bone 12 and are deformed to the reduced diameter state engaging the interior surface of the cavity 16. In embodiments, one or more of the fingers 72 may be resilient, and apply forces away from the rod 18 and toward the bone 12 following insertion of the rod and centering device 22 in the cavity 16.

Figure 7:
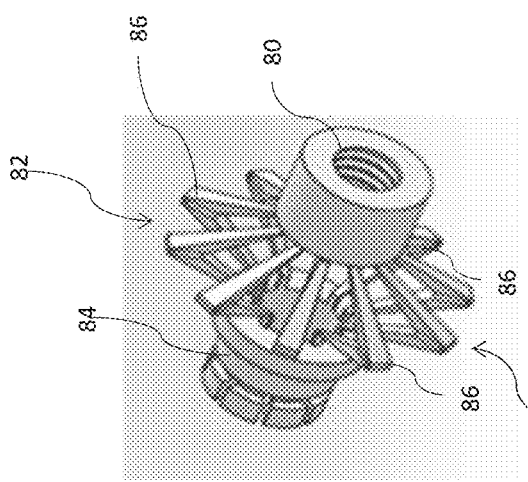
FIG. 7 is an isometric illustration of the centering device shown in FIGS. 6A and 6B in an enlarged diameter deployed state, in accordance with embodiments.
Figure 9:
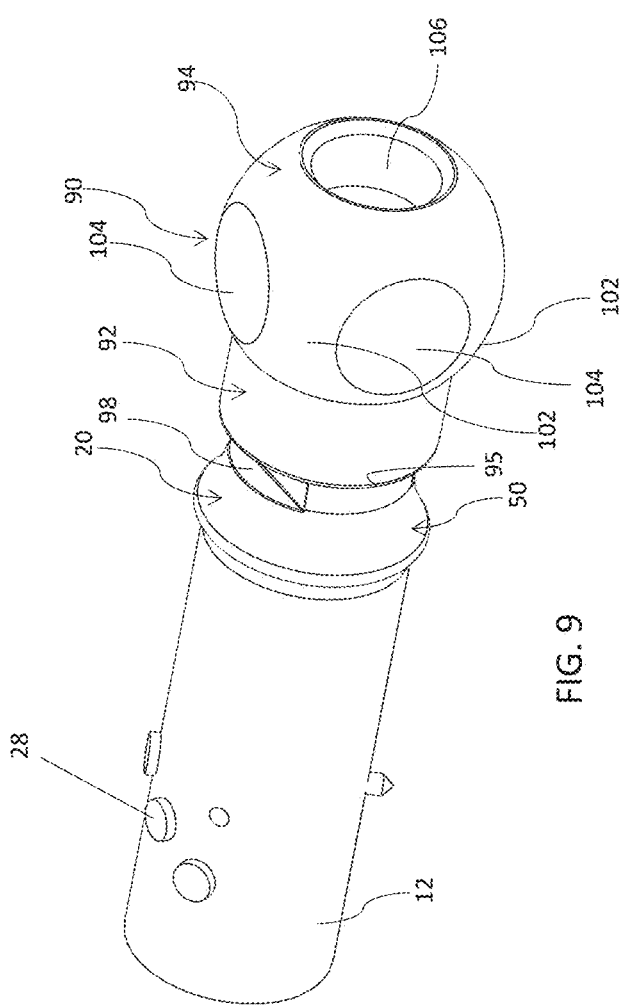
FIG. 9 is an isometric illustration of the osseointegration system shown in FIG. 1, including an end cap on the implant in accordance with embodiments, shown with the osseointegration system mounted to the bone of the patient.
Figure 10:
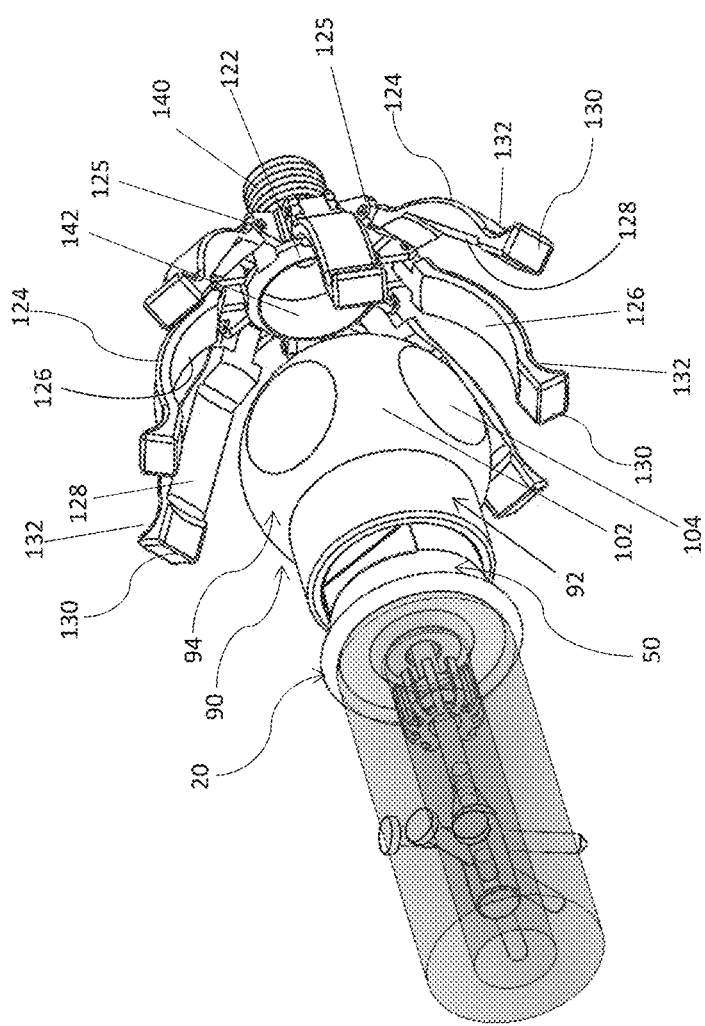
FIG. 10 is an isometric illustration of the osseointegration system shown in FIG. 9, including a coupling device that can be mounted to the implant, in accordance with embodiments, shown with the osseointegration system mounted to the bone of the patient.

FIGS. 6A, 6B, 7 and 8 are illustrations of a centering device 22' in accordance with other embodiments on the rod 18. The centering device 22' is shown in a reduced diameter, undeployed state in FIGS. 6A, 6B and 8, at which it can be inserted into the cavity 16 of the bone 12. FIG. 7 is an isometric illustration of the centering device 22' in an enlarged diameter, deployed state. The centering device 22' is configured to diametrically adjust by expanding from the reduced diameter state shown in FIGS. 6A, 6B and to the enlarged diameter state shown in FIG. 7 after insertion of the rod 18 and centering device into the cavity 16 of the bone 12. In the illustrated embodiments the centering device 22' includes a first end portion 80 configured to be mounted to the rod 18, a diametrically expandable member 82 mounted to the first end portion, and a second end portion 84 mounted to the diametrically expandable member opposite the first end portion. In the illustrated embodiments the first end portion 80 is a threaded member configured to be screwed onto and positioned at a desired location along the length of the threaded rod 18. Other embodiments include other structures for fastening the first end portion 80 to the rod 18.

The second end portion 84 is configured to move along the rod 18 with respect to the first end portion 80. When the centering device 22' is in the undeployed state, the second end portion 84 is located at a first distance from the first end portion 80. When the undeployed centering device 22' is placed on the rod 18 and the rod and undeployed centering device are inserted into the cavity 14 of the bone, the first end portion 80 and second end portion 84 may remain located at the first distance from one another. The illustrated embodiments of the diametrically expandable member 82 include a plurality of deformable members 86 extending between the first and second end portions 80 and 84 at circumferentially spaced locations around the first and second end portions. The diametrically expandable member 82 thereby defines a tubular or sleeve-like structure that surrounds a length of the rod 18 when the centering device 22' is mounted to the rod 18. After the rod 18 including the centering device 22' is inserted into the cavity 16 of bone 12 with the centering device in its reduced diameter state, a deployment member such as threaded nut 88 (FIG. 6B) can be screwed onto the rod and engaged with the second end portion 84. With continued advancement of the threaded nut 88 along the rod 18 while the first end portion 80 is at a fixed position, the threaded nut forces and moves the second end portion 84 toward the first end portion, and thereby causes the deformable members 86 to bow or otherwise extend radially outwardly and diametrically expand toward the expanded diameter state shown in FIG. 8, and into engagement with the interior of the cavity 16. The threaded nut 88 also functions as a clamping member to retain the second end portion 84 at the position that it was moved to with respect to the first end portion 80, and retain the centering device 22' in its diametrically expanded state. Centering devices can be formed from any suitable materials, including metals and polymers.

Other embodiments include other structures for causing the deformable members 86 to diametrically expand and/or to retain the centering device 22' in its expanded state. For example, in embodiments a locking sleeve can replace the threaded nut 88, and the locking sleeve is slid along the rod 18 and over the second end portion 84 to push the second end portion and to retain it in place.

FIGS. 9-11, 12A and 12B illustrate an end cap 90 that can be mounted to the implant 20. The illustrated embodiments of end cap 90 seal the implant 20 and enable peripheral devices, such as prosthetic limbs, to be mounted to the implant. As shown, the end cap 90 includes an implant mounting portion 92 and a coupling device mounting portion 94. The implant mounting portion 92 is a generally tubular member and includes an open proximal end 95 and a generally cylindrical inner surface 96. In embodiments, the inner surface 96 tapers in a direction toward a center of the implant mounting portion 92 with increasing distance from the proximal end 95 (i.e., the inner diameter of the implant mounting portion decreases with increasing distance from the open proximal end). In embodiments, the tapered inner surface 96 of the implant mounting portion 94 is complimentary to the tapered outer surface 56 of the implant 20 (FIG. 1) to provide a mounting system, such as a Jacobs or other machine taper, to secure the end cap 90 to the implant 20. By the machine taper mounting system, the implant mounting portion 92 of the end cap 90 can be frictionally engaged with mounting portion 52 of the implant 20. In other embodiments the end cap 90 and/or implant 20 are configured with other structures enabling them to be mounted to one another. In the embodiments shown in FIGS. 12A and 12B, the proximal end 95 of the end cap 90 extends proximally over recesses 98 in the base portion 50 of the implant 20, thereby providing structures that can be used to remove the end cap from the implant, if desired.

FIGS. 10, 11, 12A and 12B illustrate a coupling device 120 that is configured to be releasably coupled to the implant 20 in accordance with embodiment. In the illustrated embodiments the coupling device 120 mounts to the implant 20 via the end cap 90, although in other embodiments the coupling device and implant 20 can be configured to be directly mounted to one another. As described in greater detail below, the coupling device 120 can be a component of a peripheral device, such as a limb or other prosthesis.

Coupling device mounting portion 94 of the end cap 90 is configured to receive the coupling device 120 in the illustrated embodiments. Coupling device mounting portion 94 is a generally spherical member that includes convex surface portions 102 and flat surface portions 104 on the sides of the mounting portion (i.e., facing generally perpendicular to the longitudinal axis of the implant 20 and end cap 90). The illustrated embodiments include four convex surface portions 102 spaced apart from one another by about 90° around the longitudinal axis of the coupling device mounting portion 94, and four flat surface portions 104 spaced apart from one another by about 90° around the longitudinal axis of the coupling device mounting portion. Each of the flat surface portions 104 is located between two of the convex surface portions 102. In other embodiments, the above-described surface configurations of the coupling device mounting portion 94 are located on the mounting portion 52 of the implant 20. Yet other embodiments of these types have other surface configurations (e.g., no or different numbers of convex surface portions 102 and/or no or different numbers of flat surface portions 104). The illustrated embodiment of end cap 90 also includes a recess 106 in its distal end.

Coupling device 120 includes a base 122 and a plurality of fingers 124. The fingers 124 are elongated members in the illustrated embodiments, and have first ends pivotally mounted to the base 122 by pivot mechanisms such as hinges 125. The fingers 124 extend radially from the base 122 in a circumferential arrangement, and are configured to move about the hinges 125 between outer, release positions such as those shown in FIG. 10 enabling receipt of the end cap 90 by the coupling device 120, and engaged positions such as those shown in FIGS. 11, 12A and 12B extending over and engaging the coupling device mounting portion 94 of the end cap. The illustrated embodiment includes four fingers 124 having concave interior surface portions 126 configured to engage and mate with the four convex surface portions 102 of the end cap 90, and four fingers 124 having recessed flat interior surface portions 128 configured to engage and mate with the four flat surface portions 104 of the end cap. Other embodiments include other configurations and arrangements of fingers or other members to cooperate with other configurations of the end cap or implant such as those described above.

Figure 11:
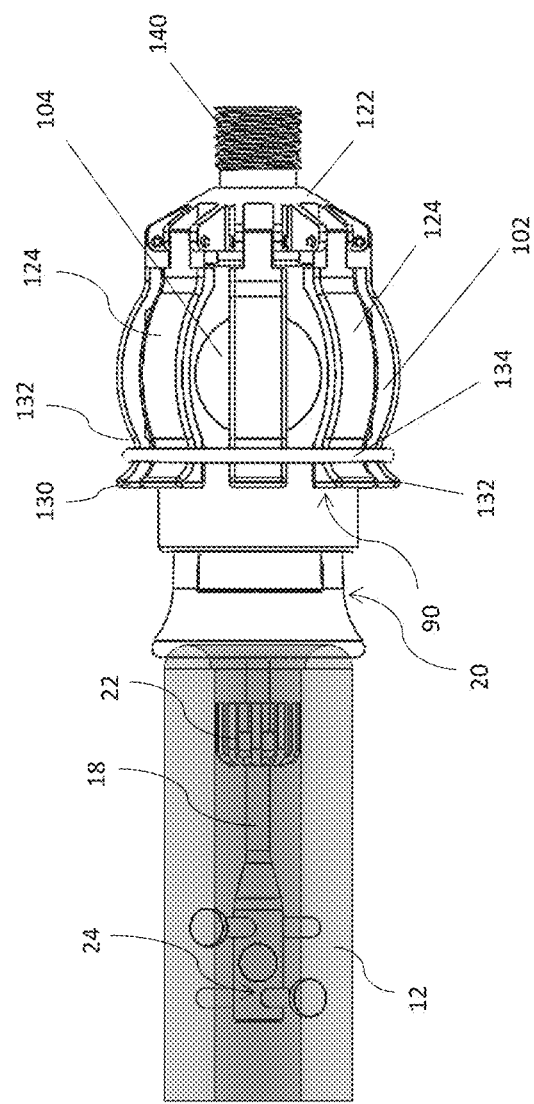
FIG. 11 is a side view of the osseointegration system shown in FIG. 10, shown with the coupling device mounted to the implant.

Distal end portions 130 of the fingers 124 include grooves or recesses 132 for receiving one or more resilient bands 134 such as those shown in FIG. 11. Although one band 134 is shown in FIG. 11, other embodiments include two or more bands. Bands 134 are elastic members that bias the fingers 124 into engagement with the coupling device mounting portion 94 of the end cap 90 to releasably secure the coupling device, and any prosthesis or other peripheral device mounted thereto, to the implant 20. The forces applied by the one or more bands 134 (each of which may apply different bias forces to allow selection of the bias forces), in conjunction with the configurations of the coupling device mounting portion 94 and fingers 124, control the force by which the coupling device 120 is engaged with the implant 20. In response to torque and/or other forces applied by the coupling device 120 to the implant 20 (e.g., that may result in damage to the implant and/or bone 20 to which the implant is mounted), the fingers 124 will radially or diametrically expand against the forces of the bands, and the bands will expand, break or otherwise release, and allow the coupling device to detach from the implant. In other embodiments, the recesses 132 that receive the bands 134 are located at other positions on the fingers 124.

Yet other embodiments include other structures for biasing the fingers 124 into engagement with the implant 20. For example, embodiments may include springs at the ends of the fingers adjacent to the hinges 125 (not shown). Additionally or alternatively, embodiments may include complimentary magnetic elements (i.e., oppositely poled magnets, or magnets and ferro magnetic elements) on the coupling device 120 and end cap 90 to magnetically (and releasably) attach the coupling device to the mounting portion 94. For example, complimentary magnetic elements (not shown) can be attached (e.g., by threaded fasteners) to the end cap 90 in the recess 106 and to the base 122 of the coupling device 120 to provide magnetic forces causing the base to engage the end cap. Alternatively or in addition, complimentary magnetic elements (not shown) can be attached to the end cap 90 and to the fingers 124 to provide magnetic forces causing the fingers to engage the end cap.

Coupling device 120 includes an attachment structure 140 on the base 122. The attachment structure 140, which is a threaded shaft in the illustrated embodiments, is configured to be mounted to other devices (not shown) such as leg, arm or other prostheses. In other embodiments the coupling device 120 is configured for other osseointegration applications, such as for fixation of an endoprosthetic in the host bone. Base 122 may also include a cap member 142 that is configured to be received in and to close the recess 106 on the end of the end cap 90.

Figure 13:
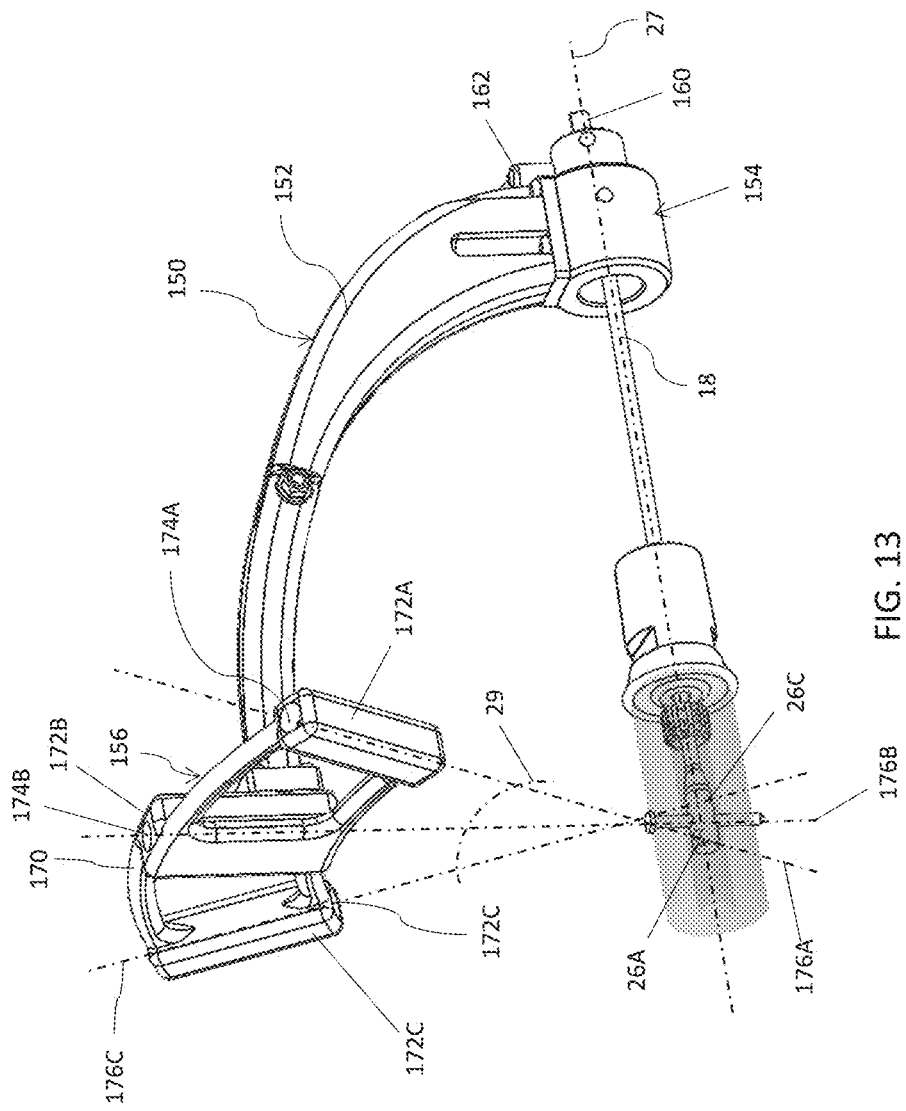

FIGS. 13-15 illustrate an aiming arm 150 that can be used to implant components of osseointegration system 10 in accordance with embodiments. Portions of the osseointegration system 10, including the rod 18 and its mounting portion 24, are shown mounted to the aiming arm 150 in FIGS. 13-15 for purposes of illustration. As shown, the aiming arm 150 includes a body or frame 152, a rod engagement structure 154, and a drill guide structure 156. Rod engagement structure 154 is located on a first end of the frame 152 and includes an aperture 158 configured to receive a distal end portion 160 of the rod 18, and a clamp 162 to clamp the distal end portion of the rod to the aiming arm 150. Clamp 162 includes a lever 164 that can be actuated by an operator to cause the clamp to engage and release the rod 18. The rod engagement structure 154 and/or the rod 18 include structure or indicia that enable and/or cause the rod engagement structure to receive the rod at a predetermined axial position along its longitudinal axis 27 and at a predetermined orientation about its circumferential axis 29. The rod 18 is thereby registered and seated at a predetermined location on the aiming arm 150.

Figure 17:
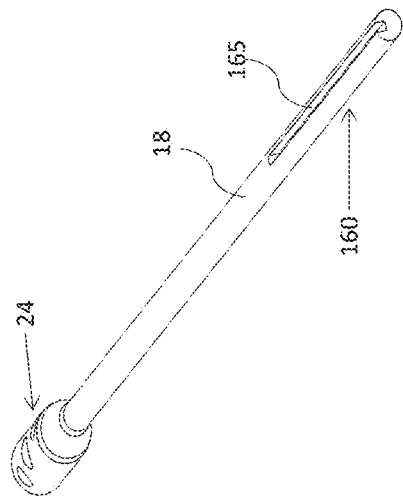
FIG. 17 is an illustration of a distal end portion of the rod, configured for cooperative engagement with the rod engagement structure shown in FIG. 16, in accordance with embodiments.
Figure 16:
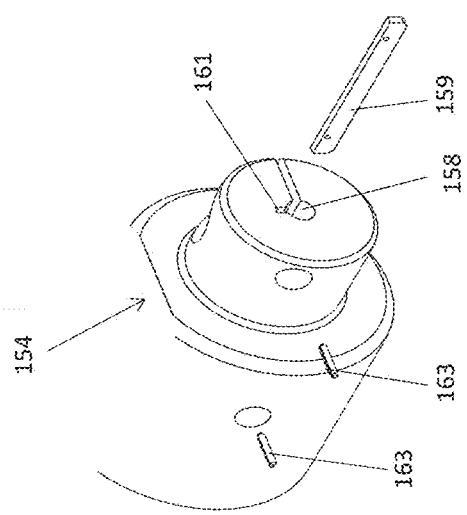
FIG. 16 is an exploded detailed view of a rod engagement structure of the aiming arm shown in FIGS. 13 and 14, in accordance with embodiments.

FIG. 16, for example, is an exploded view of a keyway structure in the rod engagement structure 154, showing the aperture 158 and an elongated key 159 that extends into the aperture. The key 159 is retained within a slot 161 by pins 163 in the illustrated embodiment. FIG. 17 illustrates an elongated, longitudinally-oriented slot 165 in the distal end portion 160 of the rod 18. The aperture 158 and key 159 of the rod engagement structure 154, and the rod 18 and its slot 165, are configured such that the rod can be inserted only at the proper rotational orientation and to the proper distance to cause three drill guides 172A-172C of the drill guide structure 156 to colinearly align with the three apertures 26A-26C, respectively, in the rod. Other embodiments of the aiming arm 150 (not shown) may have other structures and/or indicia for registering and seating the rod 18 at a predetermined location and orientation.

Drill guide structure 156 includes a frame 170 that supports the three drill guides 172A-172C. The drill guides 172A-172C include elongated guide apertures 174A-174C, respectively. Longitudinal axes 176A-176C of the guide apertures 174A-174C are illustrated in FIGS. 13 and 14. Frame 170 positions the drill guides 172A-172C at positions with respect to the longitudinal axis 27 and rotational axis 29 that cause the longitudinal axes 176A-176C of the drill guides 172A-172C to be colinear with the apertures 26A-26C respectively, through the mounting portion 24 of the rod 18 when the rod is registered and seated at the predetermined location and orientation on the aiming arm 150. One or more structural and/or positional relationships of the rod 18, frame 152, engagement structure 154 and drill guide structure 156 can be configured to provide the colinear relationships between the guide apertures 174A-174C and apertures 26A-26C of the rod 18. Other embodiments of aiming arm 150 (not shown) may have more or fewer drill guides.

Figure 12:
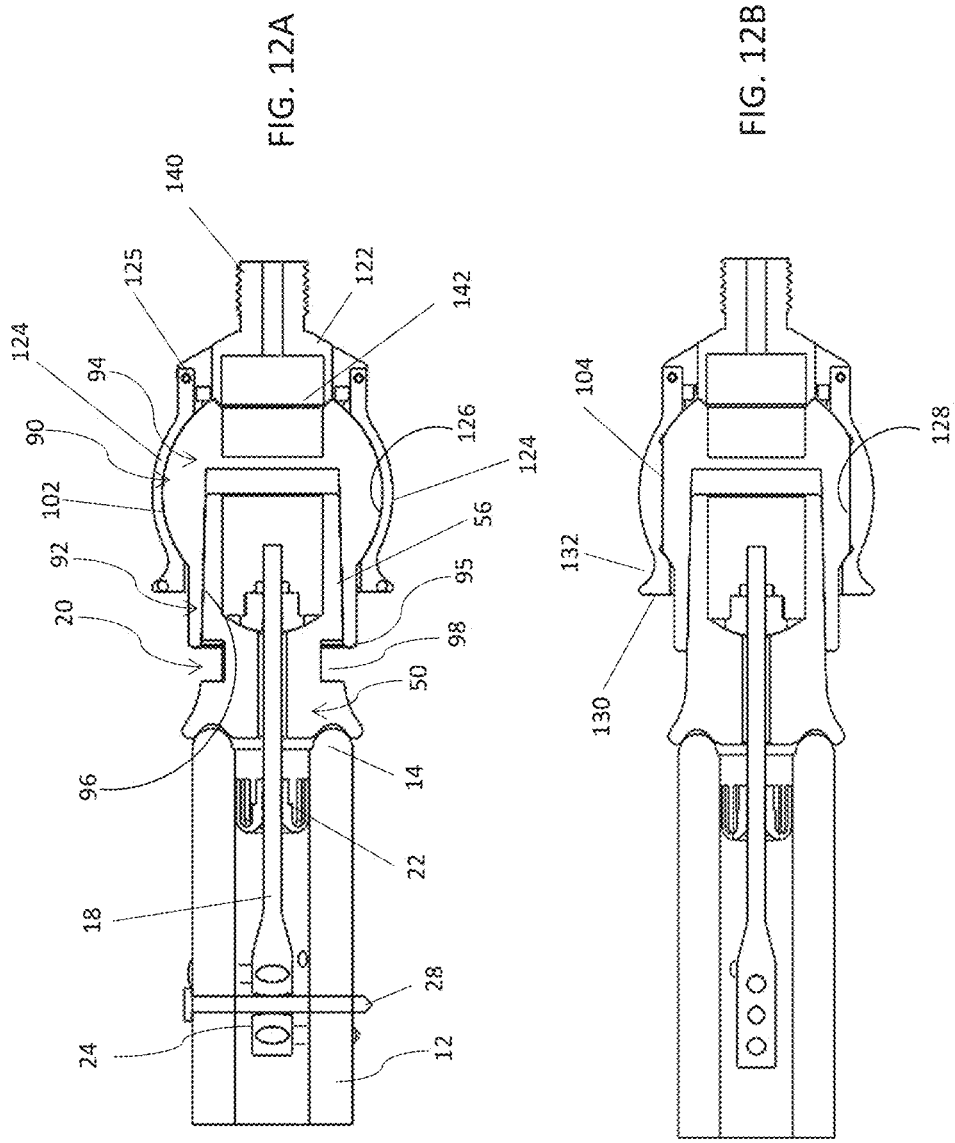
FIGS. 12A and 12B are cross sectional side views of the osseointegration system shown in FIG. 11, shown with the coupling device mounted to the implant.

A method by which the osseointegration system 10 can be implanted into the bone 12 of a patient using the aiming arm 150 can be described with reference to FIGS. 1-5, 6A, 6B, 7-11, 12A, 12B and 13-15. In embodiments, the distal end 14 of the bone 12 may be prepared to enhance mating with the proximal end surface 36 of the implant 20. For example, in embodiments of the implant 20 including an annular recess such as 54 on the proximal end surface 36, the distal end 14 of the bone 12 may be reamed to provide a convex end surface (e.g., as shown in FIGS. 1, 12A and 12B). In embodiments, the centering device 22 or 22' is placed at a location on the rod 18 that will be within the cavity 16 of the bone 12 at a relatively short distance such as 1 cm from the prepared end 14 of the bone. Placement in this manner can help a surgeon gauge the depth of insertion of the rod 18 into the bone 12. In embodiments, for example, the centering device 22 or 22' can be threaded to the desired location on the rod 18 based on the planned depth of placement. When using centering device 22', the threaded nut 88 may be placed adjacent to the centering device, but not engaging or deploying the centering device 22' (e.g., as shown in FIG. 6B) prior to implantation of the rod 18.

The rod 18 with the centering device 22 or 22' thereon can then be registered and seated on the aiming arm 150 with the distal end portion 160 of the rod in the rod engagement structure 154 (e.g., as shown in FIG. 13). As described above, in embodiments including the cooperating rotational and length registration structures or indicia on the rod 18 and/or aiming arm 150, the rod may be registered and seated to locate its mounting portion 24 at the predetermined orientation and location with respect to the drill guide structure 156. The clamp 162 may then be actuated to lock the rod 18 to the aiming arm 150. Proper placement of the rod 18 on the aiming arm 150 can be checked and confirmed by placing drill guide cannulas (not shown) through the guide apertures 174A-174C of the drill guide structure 156 and ensuring that they are aligned with the corresponding apertures 26A-26C on the rod. The implant 20 may or may not be positioned on the rod 18 when the rod is mounted to the aiming arm 150.

The rod 18 is inserted into the cavity 16 to the desired depth in the bone 12 (e.g., as shown in FIG. 13). When the system 10 is used with small bones 12, the bone cortex may be reamed to about 10 mm to allow passage of the rod 18. In embodiments including the centering device 22 on the rod 18, during this rod insertion step the fingers 72 will deform by engagement with the bone 12 and cause the centering device 22 to take its deployed state in the bone (e.g., as shown in FIG. 2).

With the mounting portion 24 of the rod 18 placed at its desired location, the bone 12 can be prepared to receive the one or more pins 28. A drill guide cannula (not shown) may be placed into one of the guide apertures 174A-174C corresponding to a first pin 28 to be inserted. When implanting embodiments of the rod 18 including an aperture such as 26B that accommodates angular positioning of the rod, the drill guide cannula may be placed into the associated guide aperture such as 174B. A hole is then drilled through both cortices of the bone 12 using a drill bit (not shown) and the drill guide cannula as a guide. The drill bit may be left in the bone 12 to provide provisional fixation of the rod 18. In embodiments including the centering device 22', the centering device may be expanded to its deployed state into engagement with the bone 12 and secured by the threaded nut 88 (e.g., as shown in FIGS. 6B and 7).

Placement of the pins 28 may proceed after the rod 18 is placed and centered. In embodiments, using a second drill bit (not shown) holes are drilled through the bone 12 for any additional apertures such as 26A and 26C using the corresponding drill guides such as 172A and 172C. Pins 28 may then be placed into the bone 12 through any such additional holes and apertures such as 26A and 26C in the rod 18. The drill bit used to drill the first hole (e.g., for the aperture 26B in the embodiments described above) may then be removed, and a pin 28 may then be placed into the bone 12 through the holes in the bone and the aperture. In embodiments, the pins 28 are screws having threaded distal ends (not shown), and the threaded ends are screwed into the bone 12 to secure the pins in place. In other embodiments, the one or more pins 28 are placed into the bone 12 and mounting portion 24 of the rod 18 and/or the associated holes drilled in the bone by other sequences or approaches.

The aiming arm 150 may be removed from the rod 18 after the rod is mounted to the bone 12 by the one or more pins 28. A shear or other tool (not shown) may be used to cut any excess length of the rod 18 from the portion mounted to the bone 12 (e.g., so the end of the cut rod is within the mounting portion 52 of the implant 20). If appropriate and not already done, the end 14 of the bone 12 may be prepared, for example reamed with a planar to create a convex surface.

The implant 20 may then be placed over the rod 18 (i.e., with the rod extending through the aperture 34), and slid over the rod to seat the proximal end surface 36 of the implant on the end 14 of the bone 12. In embodiments, the groove 54 on the base portion 52 of the implant is engaged with the edge on the end 14 of the bone 12 (e.g., as shown in FIGS. 1, 12A, 12B). First nut 38 is then threaded onto the rod 18 and its proximal end face 40 engaged with the surface 42 of the implant 20. The configurations of these components provides a limited (e.g., +/−7.5 degrees) range of motion between the rod 18 and implant 20 to enhance (e.g., ensure full) seating of the implant against the cortical surface of the bone 12. First nut 38 is then torqued to provide compression of the implant 20 with respect to the bone 12. Locking nut 60 may then be threaded onto the rod 18 and engaged with the first nut 38 to prevent loss of compression (e.g., as shown in FIG. 1).

End cap 90 may then be mounted to the implant 20. In the embodiments described above, the end cap 90 is mounted to the implant 20 by the Jacob's taper machine taper mounting system provided by the surface 56 on the implant and the surface 96 on the end cap. By the embodiments described herein, the end cap 90 seals the inner workings of the implant 20 (e.g., the nuts 38 and 60 and rod 18) from the external environment.

Attachment of peripheral devices such as prosthetic limbs may be done after the implant 20 has healed to the bone 12. In embodiments, the coupling device 120 is mounted to the implant 20 (e.g., via the end cap 90 in the illustrated embodiments) by moving the fingers 124 radially outwardly from the base 122 to diametrically expand an opening defined by the distal ends 130 by an amount sufficient to enable the distal ends of the fingers to move over the device mounting portion 94 of the end cap 90. The fingers 124 are then moved into engagement with the device mounting portion 94 of the end cap 90, and biased to the engaged position. In the illustrated embodiments the fingers 124 are biased into engagement with the end cap 90 by the use of one or more resilient bands 134, and the bands may be placed around the fingers before the fingers are opened to enable receipt of the end cap. The number of bands 134 and/or the amount of bias force provided by the bands can be selected to provide the desired coupling force. The peripheral devices may be mounted to the coupling device 120 though by the attachment structure 140 on the base 122 of the coupling device.

Osseointegration system 10 and the components therefore provide important advantages. For example, it can be secured to relatively small amounts of residual bone and removed without significant bone destruction. It is fully adjustable to a large range of bone sizes and lengths. It may be used on patients that would otherwise not be candidates for osseointegration. Should it be desired to remove the implant, the removal procedure can be performed relatively easily with minimal bone loss. The threaded intramedullary rod provides compression and allows for variable depths of insertion, including short segments of bone. The beveled nut and other surfaces allow the implant to self-level as compression is applied between the bone and the on-growth surface. Bone contact area can thereby be maximized. The coupling device provides an effective and adjustable torque limiting release capability to reduce the potential for damage to the implant or limb. It is compact and can be covered by a sleeve or clothing.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale but may be exaggerated to illustrate various aspects of the present disclosure, and in that regard, the drawing figures should not be construed as limiting.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. An osseointegration system, comprising:
a rod configured for placement in a bone cavity, including:
a proximal mounting portion configured to be secured to the bone in the bone cavity; and
a threaded distal portion;
an implant configured to have a peripheral device coupled thereto, including:
a first surface configured to engage an end of the bone;
a second surface; and
an aperture through the implant, wherein the aperture is configured to enable the rod to extend through the implant;
a threaded first nut, including:
a first end face;
a second end portion; and
a threaded aperture through the nut configured to be received by the threaded distal portion of the rod;
wherein the rod, implant and first nut are configured to cause the first end face of the first nut to engage the second surface of the implant and to compress the first surface of the implant onto the end of the bone when the threaded aperture of the first nut is mounted to and moved on the threaded distal portion of the rod.

2. The osseointegration system of claim 1 wherein:
the second surface of the implant tapers in a direction away from the first surface with increasing distance from the aperture through the implant; and
the first end face of the first nut tapers in a direction toward the second end portion with increasing distance on the first end face from the aperture through the first nut.

3. The osseointegration system of claim 2 wherein the second surface of the implant and the first end face of the first nut include complementary engaging surfaces.

4. The osseointegration system of claim 1 wherein a diameter of a portion of the rod extending through the aperture of the implant is less than a diameter of the aperture of the implant to allow self-centering angular motion between the implant and the rod.

5. The osseointegration system of claim 1 and further including a second nut configured to be mounted to the threaded distal portion of the rod opposite the first nut from the implant and to engage the second end portion of the first nut.

6. An osseointegration system, comprising:
a rod configured for placement in a bone cavity having a diameter, including:
a proximal mounting portion configured to be secured to the bone in the bone cavity; and
a distal portion;
an implant, including:
a proximal surface configured to engage an end of the bone;
a second surface;
an aperture through the implant, wherein the aperture is configured to enable the rod to extend through the implant;
a fastening structure to secure the implant to the distal portion of the rod, wherein the fastening structure is configured to compress the proximal surface of the implant onto the end of the bone; and
a diametrically adjustable centering device on a portion of the rod distal to the mounting portion and configured to be located within the bone cavity, wherein the centering device is configured to be adjustable between a first diameter less than or equal to the diameter of the bone cavity to a second diameter at least as great as the diameter of the bone cavity.

7. The osseointegration system of claim 6 wherein the centering device is configured to be expandable between the first diameter and the second diameter after the rod is inserted into the bone cavity.

8. The osseointegration system of claim 6 wherein the centering device is configured to be compressible from the second diameter to the diameter of the bone cavity during insertion of the centering device into the bone cavity.

9. An osseointegration system, comprising:
an implant including an outer side surface;
an osseointegration mount for mounting the implant to a bone; and
a coupling device coupled to the implant, the coupling device including:
a base;
a plurality of members extending from the base at circumferentially-spaced locations and configured to engage the outer side surface of the implant; and
one or more bias members releasably forcing the plurality of members into engagement with the outer side surface of the implant; and
wherein the outer side surface of the implant includes one or more convex surface portions; and
at least some of the members include interior concave surface portions configured to engage and mate with one of the one or more convex surface portions of the implant.

10. The osseointegration system of claim 9 wherein at least some of the members include an elongated finger.

11. The osseointegration system of claim 10 wherein each of the elongated fingers includes a proximal end portion pivotally connected to the base.

12. The osseointegration system of claim 11 wherein each of the elongated fingers includes a distal end portion.

13. The osseointegration system of claim 12 wherein:
each of the elongated fingers is configured to receive a resilient band;
and the one or more bias members includes at least one resilient band engaging the fingers to bias the fingers into engagement with the side surface of the implant.

14. The osseointegration system of claim 13 wherein the distal end portions of the fingers define a circumferential recess around an exterior of the coupling device, and wherein the circumferential recess is configured to receive the at least one resilient band.

15. The osseointegration system of claim 13 wherein the distal end portions of the fingers include recesses for receiving the at least one resilient band.

16. The osseointegration system of claim 9 wherein:
the outer side surface of the implant includes one or more flat surface portions; and at least some of the members include interior flat surface portions configured to engage and mate with one of the one or more flat surface portions of the implant.

17. The osseointegration system of claim 9 and further including a peripheral device coupled to the coupling device.

18. The implant of claim 9 wherein the implant includes an implant member and an end cap on the implant member, and wherein the coupling device is configured to engage the end cap.

* * * * *